(12) United States Patent
Shaw et al.

(10) Patent No.: US 10,625,028 B2
(45) Date of Patent: Apr. 21, 2020

(54) SAFETY SYRINGE WITH NEEDLE REDIRECTION DEVICE

(71) Applicants: Retractable Technologies, Inc., Little Elm, TX (US); Thomas J. Shaw, Frisco, TX (US)

(72) Inventors: Thomas J. Shaw, Frisco, TX (US); Mark Small, Heavener, OK (US)

(73) Assignee: Retractable Technologies, Inc., Little Elm, TX (US)

( * ) Notice: Subject to any disclaimer, the term of this patent is extended or adjusted under 35 U.S.C. 154(b) by 137 days.

(21) Appl. No.: 15/635,346

(22) Filed: Jun. 28, 2017

(65) Prior Publication Data

US 2019/0001075 A1 Jan. 3, 2019

(51) Int. Cl.
*A61M 5/32* (2006.01)
*A61M 5/50* (2006.01)
*A61M 5/315* (2006.01)

(52) U.S. Cl.
CPC ...... *A61M 5/3278* (2013.01); *A61M 5/31505* (2013.01); *A61M 5/3216* (2013.01); *A61M 5/3245* (2013.01); *A61M 5/50* (2013.01); *A61M 5/31513* (2013.01); *A61M 5/3202* (2013.01); *A61M 2005/3151* (2013.01); *A61M 2005/31506* (2013.01); *A61M 2005/31508* (2013.01); *A61M 2005/3217* (2013.01); *A61M 2005/3284* (2013.01); *A61M 2205/0216* (2013.01); *A61M 2205/273* (2013.01)

(58) Field of Classification Search
CPC ........ A61M 2005/3284; A61M 5/3278; A61M 5/3216; A61M 5/322; A61M 2005/3249; A61M 5/50; A61M 5/3224; A61M 5/321
See application file for complete search history.

(56) References Cited

U.S. PATENT DOCUMENTS

| | | | | |
|---|---|---|---|---|
| 3,712,302 | A * | 1/1973 | Burke | A61M 5/3213 225/5 |
| 4,188,950 | A * | 2/1980 | Wardlaw | A61M 5/2033 604/111 |
| 4,266,544 | A | 5/1981 | Wardlaw | |
| 5,151,089 | A | 9/1992 | Kirk, III et al. | |
| 5,158,550 | A * | 10/1992 | Scholl, Jr. | A61M 5/002 604/110 |
| 5,554,126 | A * | 9/1996 | Filley | A61M 5/3213 604/110 |
| 6,530,903 | B2 | 3/2003 | Wang et al. | |
| 6,761,705 | B1 | 7/2004 | Chiu | |
| 9,138,545 | B2 | 9/2015 | Shaw et al. | |

(Continued)

FOREIGN PATENT DOCUMENTS

WO    WO2005032629    4/2005

*Primary Examiner* — Nathan R Price
*Assistant Examiner* — Melissa A Snyder
(74) *Attorney, Agent, or Firm* — Ross Barnes LLP; Monty L. Ross

(57) ABSTRACT

A safety syringe comprising a needle redirection device that is desirably configured to bend the needle shaft forwardly of the barrel following an injection to thereby redirect the needle tip from a first position where it projects forwardly in coaxial alignment with the syringe barrel to a second position where the needle tip is covered or protected from incidental or accidental contact and associated needle sticks. Both sliding and pivoting embodiments are disclosed.

21 Claims, 11 Drawing Sheets

(56) References Cited

U.S. PATENT DOCUMENTS

| | | | |
|---|---|---|---|
| 9,308,353 B2 | 4/2016 | Shaw et al. | |
| 9,320,469 B2 | 4/2016 | Shaw et al. | |
| 9,381,309 B2 | 7/2016 | Shaw et al. | |
| 9,457,155 B2* | 10/2016 | Mathiasson | A61M 5/3216 |
| 2002/0038111 A1* | 3/2002 | Alchas | A61M 5/46 |
| | | | 604/500 |
| 2002/0165498 A1 | 11/2002 | Ward, Jr. | |
| 2004/0186427 A1 | 9/2004 | Pok | |
| 2009/0204026 A1 | 8/2009 | Crawford et al. | |
| 2009/0292249 A1* | 11/2009 | Moberg | A61M 25/02 |
| | | | 604/164.08 |
| 2011/0224626 A1* | 9/2011 | Lin | A61M 5/3213 |
| | | | 604/263 |
| 2011/0319831 A1* | 12/2011 | Bode | A61M 5/3202 |
| | | | 604/192 |
| 2012/0323216 A1 | 12/2012 | Koh | |
| 2014/0012206 A1* | 1/2014 | Shaw | A61M 5/3221 |
| | | | 604/198 |
| 2014/0171876 A1 | 6/2014 | Shaw et al. | |
| 2016/0310057 A1 | 10/2016 | Shaw et al. | |
| 2016/0310677 A1 | 10/2016 | Shaw et al. | |
| 2016/0310705 A1 | 10/2016 | Shaw et al. | |
| 2016/0317756 A1 | 11/2016 | Shaw et al. | |
| 2018/0126093 A1* | 5/2018 | Tuttle | B21G 1/08 |

* cited by examiner

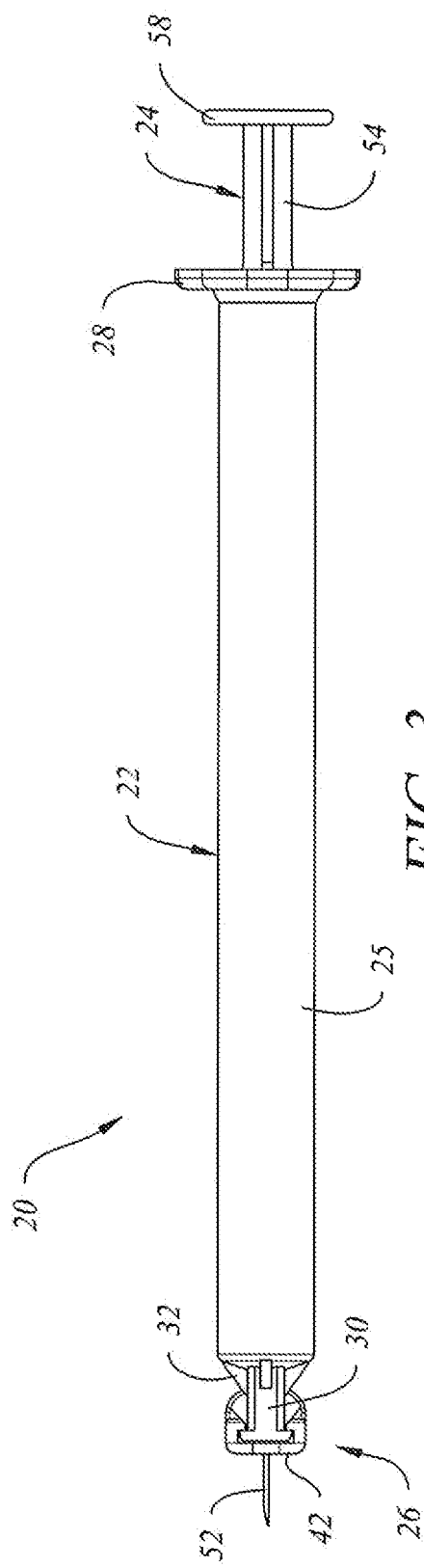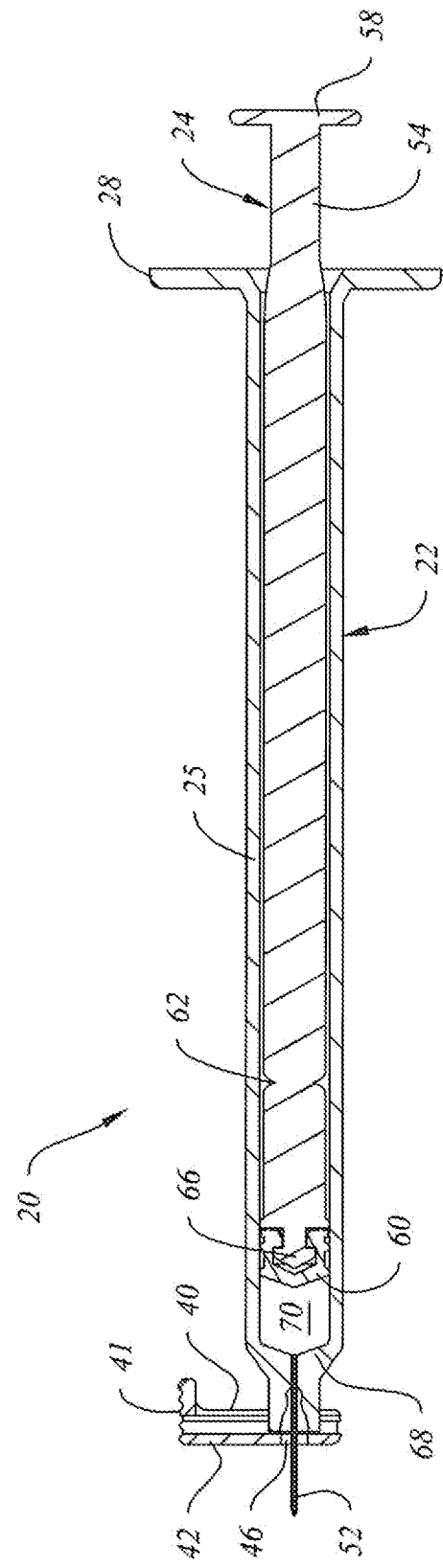

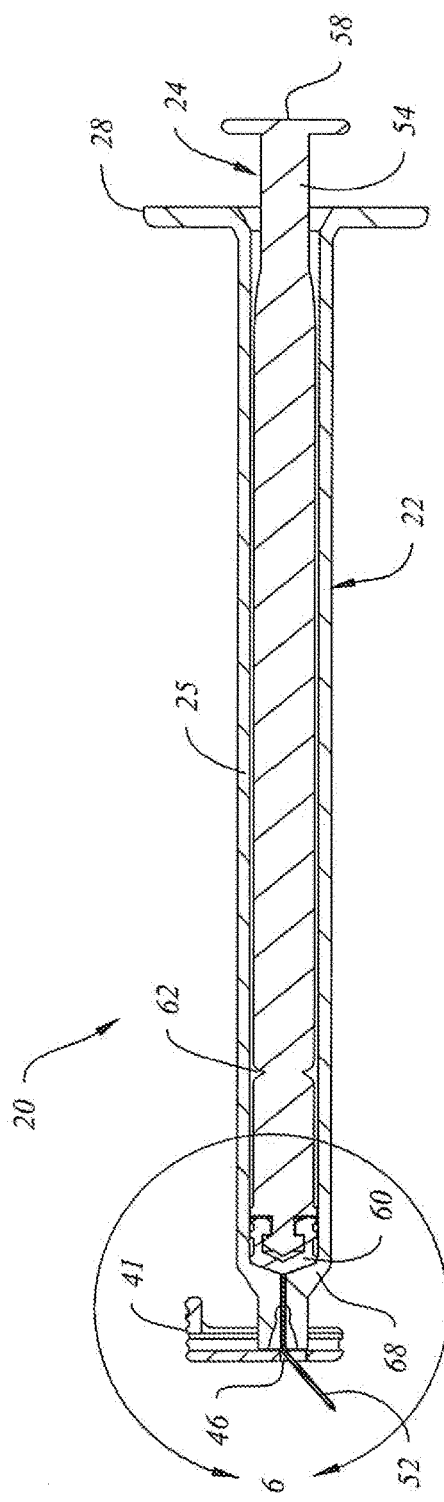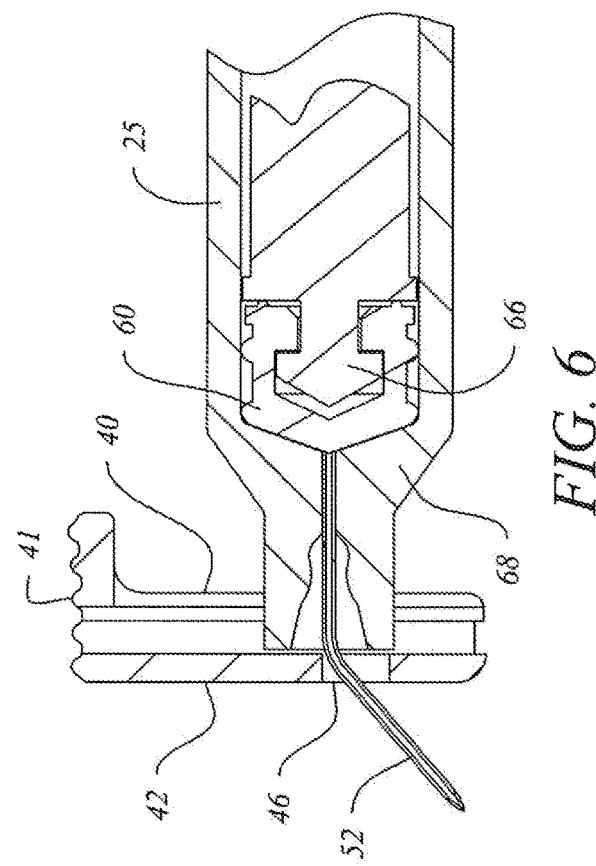
FIG. 5
FIG. 6

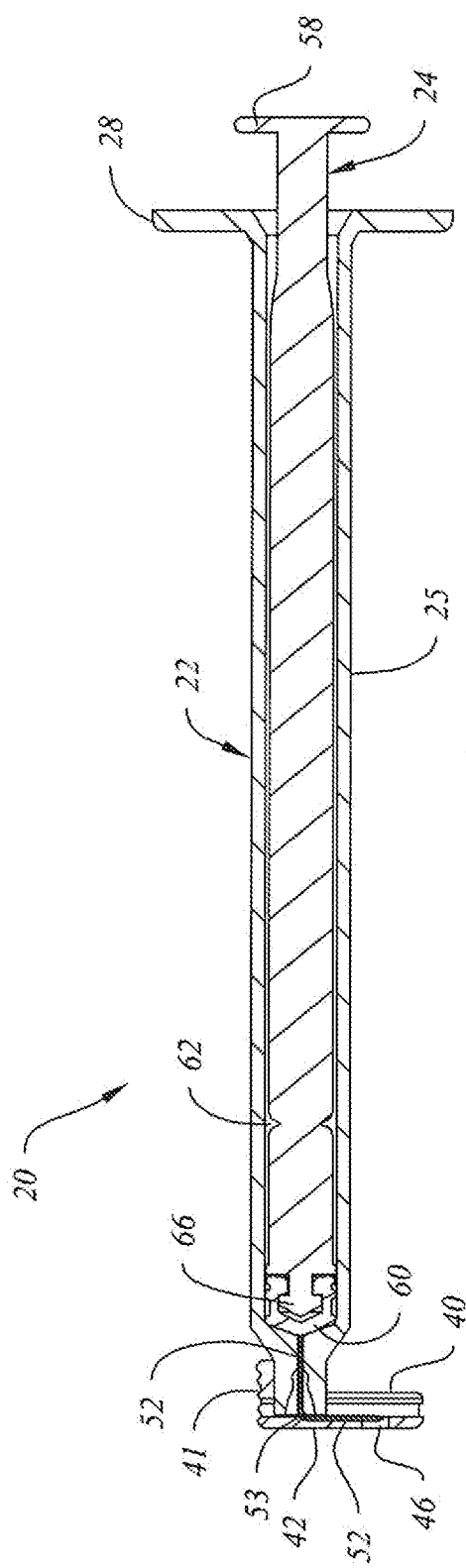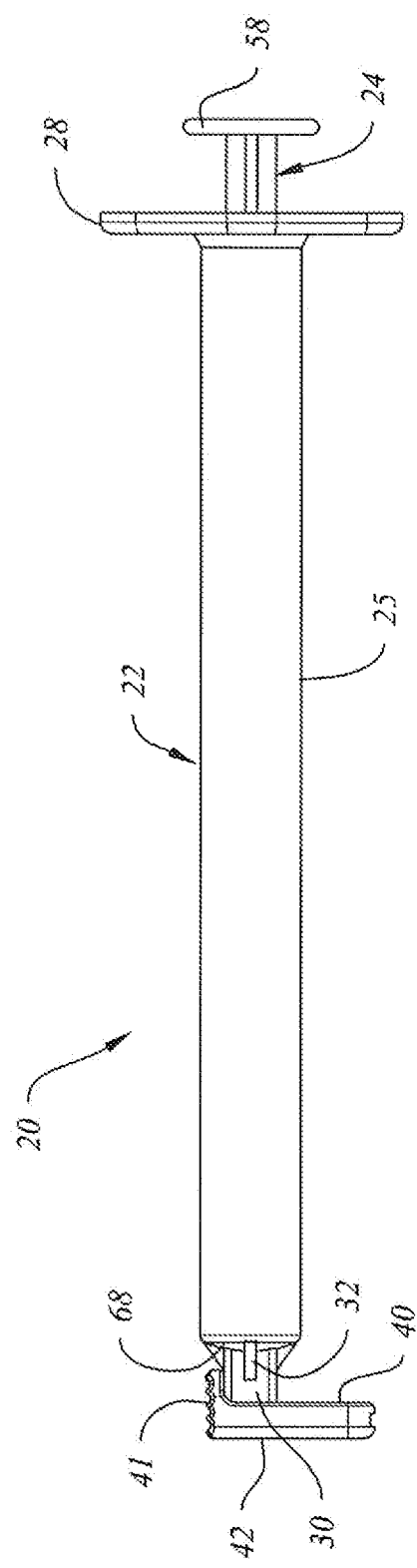
FIG. 7
FIG. 8

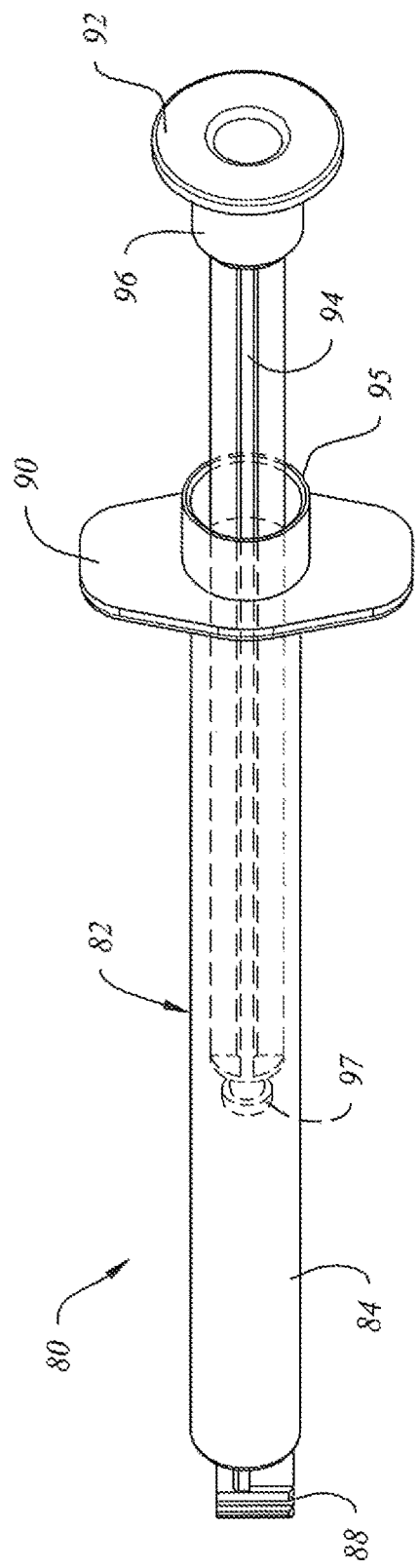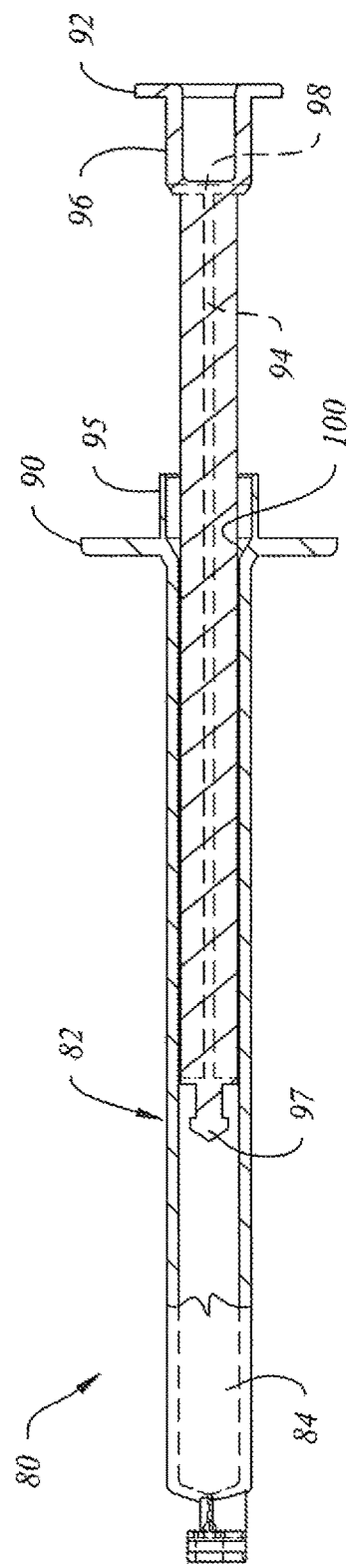
FIG. 12
FIG. 13

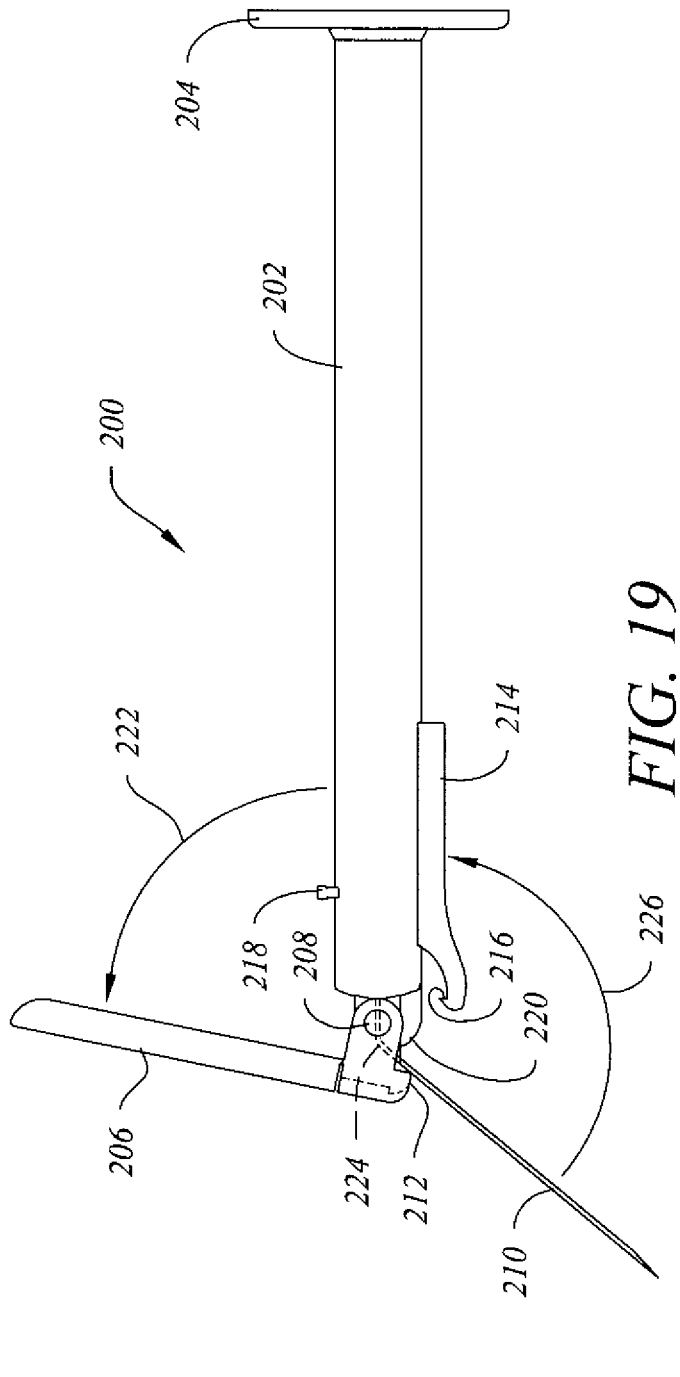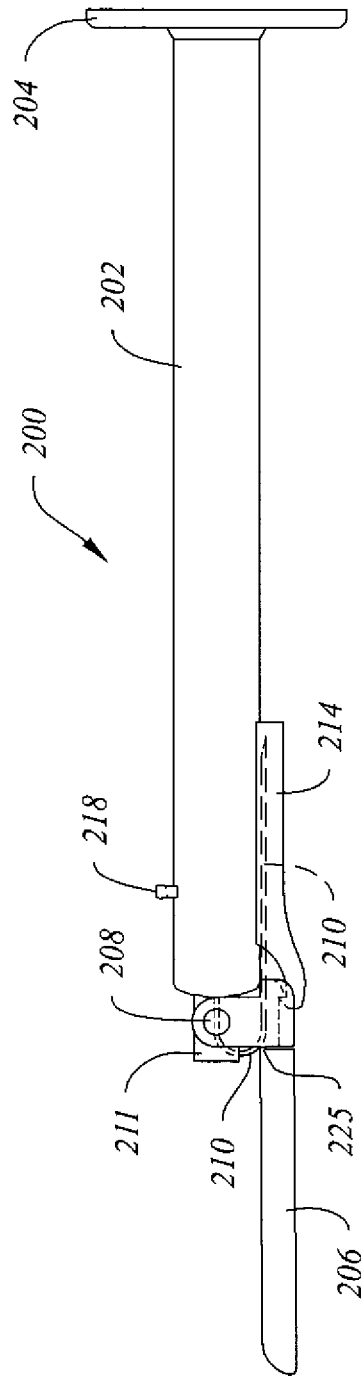

SAFETY SYRINGE WITH NEEDLE REDIRECTION DEVICE

FIELD OF THE INVENTION

This invention relates to a non-reusable safety syringe having a needle redirection device that is used to bend, redirect and protect the needle following use. One aspect of the invention relates to safety syringes having relatively short and small diameter needles that are useful for administering low-volume injections or infusions of not more than about 1 mL, and that are particularly suitable for uses such as, for example, administering a subcutaneous or intradermal injection of drugs such as those used, for example, in treating diabetes or tuberculosis (TB).

Another aspect of the subject syringe relates to a safety syringe including a needle redirection device having a transversely slidable needle protection member (hereinafter referred to as "slide member") that is attached to a slide support structure on the front end portion of the barrel. The slide member desirably includes an aperture through which the needle extends forwardly prior to and during use. The slide member is desirably configured to be moved transversely relative to the longitudinal axis through the needle following an injection, thereby bending the needle shaft forwardly of the barrel and causing the needle tip to be hidden in a protected and contained or concealed position behind the slide member. Once the needle has been bent, reuse of the syringe is not possible and the likelihood of an accidental needle stick during subsequent handling or disposal of the syringe is reduced. A needle cap is also desirably provided to cover the needle tip prior to use and to prevent the slide member from sliding transversely relative to the longitudinal axis of the barrel and the needle prior to removal of the needle cap.

Still another aspect of the subject invention relates to a single-use syringe having a needle redirection device that is particularly useful with relatively longer hypodermic needle of the type used, for example, in administering intravascular or intramuscular injections. Such hypodermic needles typically range from about 0.5 inches to about 1.5 inches in length. In this embodiment of the invention, the needle redirection device desirably comprises a rotatable actuator pivotably connected to the syringe barrel that bends the forwardly projecting needle through an arc of about 180° to a rearwardly facing position inside a cradle where the needle tip is retained and protected from inadvertent contact with a patient or user.

DESCRIPTION OF RELATED ART

During the past two decades, much attention has been focused on how to reduce or prevent the spread of blood-borne pathogens arising from the reuse of hypodermic needles by and among individuals and accidental needle stick injuries experienced by medical care providers. Medical product manufacturers have in recent years developed many new "single use" or "safety" syringes that are intended to be disabled and disposed of following a single use and/or that desirably shield the needle tip against accidental or incidental contact with a patient or clinician either prior to or following an injection. Some such products utilize moveable shields or guards to cover a forwardly projecting needle following use. Other products utilize mechanisms or devices that can be activated to disrupt the fluid flow path, or to retract or withdraw a needle into a "needle retraction cavity" following use so that the needle tip no longer projects forwardly in an exposed position. Such "safety syringes" can be difficult and expensive to make, and can also be difficult to use reliably.

Conventional hypodermic needles intended for administering injections typically range up to about 1.5 inches in length. Although needles having effective lengths ranging from about 12 to 16 mm were previously provided for hypodermic syringes used in administering subcutaneous injections or intradermal injections, progressively shorter and thinner (smaller diameter) needles have become widely available in recent years and are now commonly used with insulin and in treating TB. Such needles are available in gauges ranging from about 28 to 32 and in nominal lengths ranging from about 4 to about 13 mm, with lengths less than about 0.5 inch (ranging from about 4 mm to about 8 mm) being generally preferred for many applications. Because human skin typically has a thickness of less than about 3 mm, such needles reduce the risk of unintentionally injecting medicines into intramuscular tissue without the necessity of "pinching up" the skin prior to needle insertion or else introducing the needle into the skin at a relatively low angle to avoid penetrating and discharging the medicine into muscle. Although the shorter and narrower needles typically provide less discomfort to patients receiving the injections, other issues relating to the safe disposal of such needles to prevent accidental needle stick injuries and possible reuse still remain.

Although many types of so-called "safety syringes" have been developed, only a small percentage of those have proved to be clinically effective and reliable for reducing the number of inadvertent needle sticks, and an even smaller percentage have been manufactured and sold into the principal markets for such syringes. Some "entry barriers" to the safety syringe market have historically included cost, functional reliability, the lack of realistic access to buyers of such products, and the market power and business practices of entrenched suppliers.

Syringes and other medical devices comprising a transversely slidable frontal attachment having a retractable needle seated inside it are disclosed, for example, in United States Publication Nos. 20140012206; 20160317756; 20160310705; 20160310677; 20160310057 and in U.S. Pat. Nos. 9,138,545; 9,308,353; 9,320,469; 9,381,309. In such devices, the portion of the frontal attachment comprising the entire needle is moved transversely into alignment with a needle retraction cavity into which the needle is propelled rearwardly following use by a biasing member such as a compression spring. Following needle retraction, the needle remains oriented longitudinally with the needle tip facing forwardly.

Safe, reliable and low cost syringes are needed, however, that do not require the provision or use of a compression spring or a needle retraction cavity to prevent reuse or render the needle "safe" following use. Such a syringe is disclosed here.

SUMMARY OF THE INVENTION

The present invention is a safety syringe comprising a needle redirection device that is desirably configured to bend the needle shaft forwardly of the barrel following an injection and to thereby redirect the needle tip from a first position where it is coaxially aligned with the syringe barrel prior to use to a second position where the needle tip is no longer forwardly facing. Such needle redirection disables the syringe and prevents reuse while also protecting the needle tip from incidental or accidental contact and associated needle sticks.

In one embodiment of the invention, the needle redirection device bends the forwardly projecting portion of the needle shaft and the needle tip to a position where the needle tip is substantially transverse to the syringe barrel and is covered to avoid accidentally sticking a user, patient or clinician following an injection. In this embodiment the bending force is manually applied to the needle shaft through a laterally moveable slide member. A selectively releasable, protective needle cap is desirably provided that covers the forwardly extending needle and frictionally engages either the slide member or a forwardly extending portion of the needle holder prior to use. In another preferred embodiment of the invention, the protective needle cap also desirably prevents the slide member from moving relative to the nose of the syringe barrel prior to use of the subject safety syringe.

In another embodiment of the invention, the needle redirection device comprises a slide member disposed on the front of the syringe barrel. The slide member desirably further comprises an aperture through which the needle projects forwardly from the barrel prior to use. The slide member can be moved transversely relative to the longitudinal axis through the barrel and needle by applying manual pressure to a touch surface that faces laterally outward from the nose of the barrel. The aperture has an inside diameter that is sufficiently greater than the outside diameter of the needle shaft that the forwardly projecting portion of the needle shaft can be bent transversely when contacted by the side wall of the aperture on the side from which the manual pressure is applied. As the application of pressure continues, the slide member rides or travels laterally over the bent portion of the needle shaft as the slide member moves transversely relative to the longitudinal axis of the barrel. This movement continues until the needle tip drops into and through the aperture to a position where the needle tip is held behind and protected by the slide member from accidental contact with a healthcare worker or patient. The slide member and the needle are desirably sized and cooperatively configured so that the needle tip drops through the aperture and behind the slide member before the transverse movement of the slide is halted by engagement of a stop surface of the slide member with an outside wall of the barrel.

In another embodiment of the invention, a non-reusable, small volume (rated use capacity preferably not more than about 1 mL) safety syringe is disclosed that has a relatively short, small diameter needle and that is particularly suitable for uses such as, for example, administering a subcutaneous or intradermal injection of drugs dissolved or suspended in a liquid carrier. Use of the device with needles having lengths ranging between about 13 mm and about 4 mm, and more preferably less than about 0.5 inch (between about 8 mm and 4 mm), and gauges ranging from about 28 to about 32 is preferred. The subject syringe desirably comprises a slide member that engages a front portion of the barrel and includes an aperture through which the needle extends forwardly prior to and during use. The slide member is desirably configured to be moved transversely relative to the longitudinal axis through the needle following an injection, thereby bending the needle and causing the needle tip to be hidden in a protected, non-exposed position behind the slide member. Once the needle has been bent, reuse is not possible and the likelihood of accidental needle sticks is reduced during subsequent handling or disposal of the syringe. A needle cap is also desirably provided to cover the needle tip prior to use and to prevent the slide member from sliding transversely relative to the longitudinal axis of the barrel and the needle prior to removal of the needle cap.

In another embodiment of the invention, a safety syringe is disclosed that desirably comprises a barrel having a nose end further comprising a slide support structure, a needle connected to and projecting forwardly from the nose end of the barrel, a plunger slidably disposed inside the barrel with a plunger seal establishing a fluid seal between the plunger and the inside wall of the barrel, and a slide member attached to the slide support structure. The slide member desirably comprises an aperture through which the needle projects forwardly from the barrel, and a laterally facing touch surface that is used to initiate movement of the slide member relative to the slide support structure of the barrel following an injection and removal of the needle from a patient. The distance that the needle projects forwardly past the slide support structure is desirably sufficient to penetrate the dermis during an injection. The inside diameter of the aperture through the slide member is desirably greater than the outside diameter of the needle to allow the needle to slide through the aperture as the slide member is moved laterally relative to the front end of the barrel. The sliding movement of the slide member relative to the slide support structure in a direction substantially transverse to the longitudinal axis of the barrel and needle causes the tip end of the needle to bend in the direction the slide member is traveling, which prevents reuse of the needle. The lateral range of travel of the aperture in the slide member relative to the original longitudinal axis of the needle is desirably sufficient that the needle tip is caused to slip downwardly through the aperture as the forward portion of the needle shaft bends in response to the advancing transverse movement of the slide member as a result of the digital pressure exerted upon the touch surface by the user. When the slide member and needle tip are in this position, the needle tip is desirably protected, contained and/or concealed to an extent that it no longer poses a risk of sticking the user, patient or other healthcare workers or bystanders. The slide member desirably comprises a stop surface that contacts the front portion of the barrel and prevents the slide member from moving far enough to become disengaged from the slide support structure after the needle tip is disposed rearwardly of the slide.

In another embodiment of the invention, the needle redirection device desirably comprises an actuator that is pivotably connected to the syringe barrel. When the actuator is pivoted away from the plunger and toward the forwardly projecting needle, the needle redirection device contacts and bends the forwardly projecting needle through an arc of about 180° to a rearwardly facing position where the needle rests inside a cradle disposed substantially parallel to the syringe barrel. When the needle retraction device is in the fully rotated position, a bearing surface of the actuator maintains contact with and exerts a holding force against the bent needle until an oppositely disposed square shoulder of the actuator engages two oppositely disposed hook surfaces at the forwardly extending end of the cradle. The needle tip is thereby retained inside the cradle and protected from inadvertent contact with a patient or user.

BRIEF DESCRIPTION OF THE DRAWINGS

The system and method of the invention are further described and explained in relation to the following figures of the drawings wherein:

FIG. 3 is a front elevation view of the safety syringe of FIG. 1 with the needle cap removed and the needle projecting forwardly from the barrel;

FIG. 4 is taken along line 4-4 of FIG. 9 and rotated 90° and is a cross-sectional plan view of the safety syringe of FIG. 1 prior to an injection;

FIG. 5 is taken along line 5-5 of FIG. 10 and rotated 90° and is a cross-sectional plan view of the safety syringe of FIG. 1 after the plunger is moved to its most forwardly possible position inside the barrel following an injection and the transversely slidable needle protection member is moved laterally relative to the needle, causing the needle to begin bending as pressure is applied manually to the laterally facing touch pad of the needle protection member;

FIG. 6 is an enlarged detail view taken from FIG. 5;

FIG. 7 is taken along line 7-7 of FIG. 11 and rotated 90° and is a cross-sectional plan view of the safety syringe of FIG. 5 after the transversely slidable needle protection member is moved laterally until it contacts the nose end of the barrel, at which time the needle is bent sufficiently that the needle tip is forced inside the aperture and is no longer exposed;

FIG. 8 is a plan view of the safety syringe of FIG. 7;

FIG. 12 is a rear perspective view of another embodiment of the plunger and barrel portions (minus the plunger seal) of the safety syringe of the invention with the plunger partially inserted into the barrel;

FIG. 13 is a plan view, partially in section and partially broken away, of the embodiment of FIG. 12;

FIG. 19 is an elevation view as in FIG. 18 but with the actuator being further rotated to an intermediate position where a bearing surface of the actuator has contacted and bent the needle to an intermediate position where it is no longer forwardly facing; and FIG. 20 is an elevation view as in FIG. 19 but with the actuator fully rotated 180° to a point where the actuator is facing forwardly and the needle is bent through an arc of about 180° to a rearwardly facing position where the needle rests inside a cradle disposed substantially parallel to the syringe barrel.

When the needle retraction device is in the fully rotated position as shown in FIG. 20, a bearing surface of the actuator maintains contact with and exerts a holding force against the bent needle until an oppositely disposed square shoulder of the actuator engages two oppositely disposed hook surfaces at the forwardly extending end of the cradle. The needle tip is thereby retained inside the cradle and protected from inadvertent contact with a patient or user.

DESCRIPTION OF THE PREFERRED EMBODIMENTS

Figure 1:
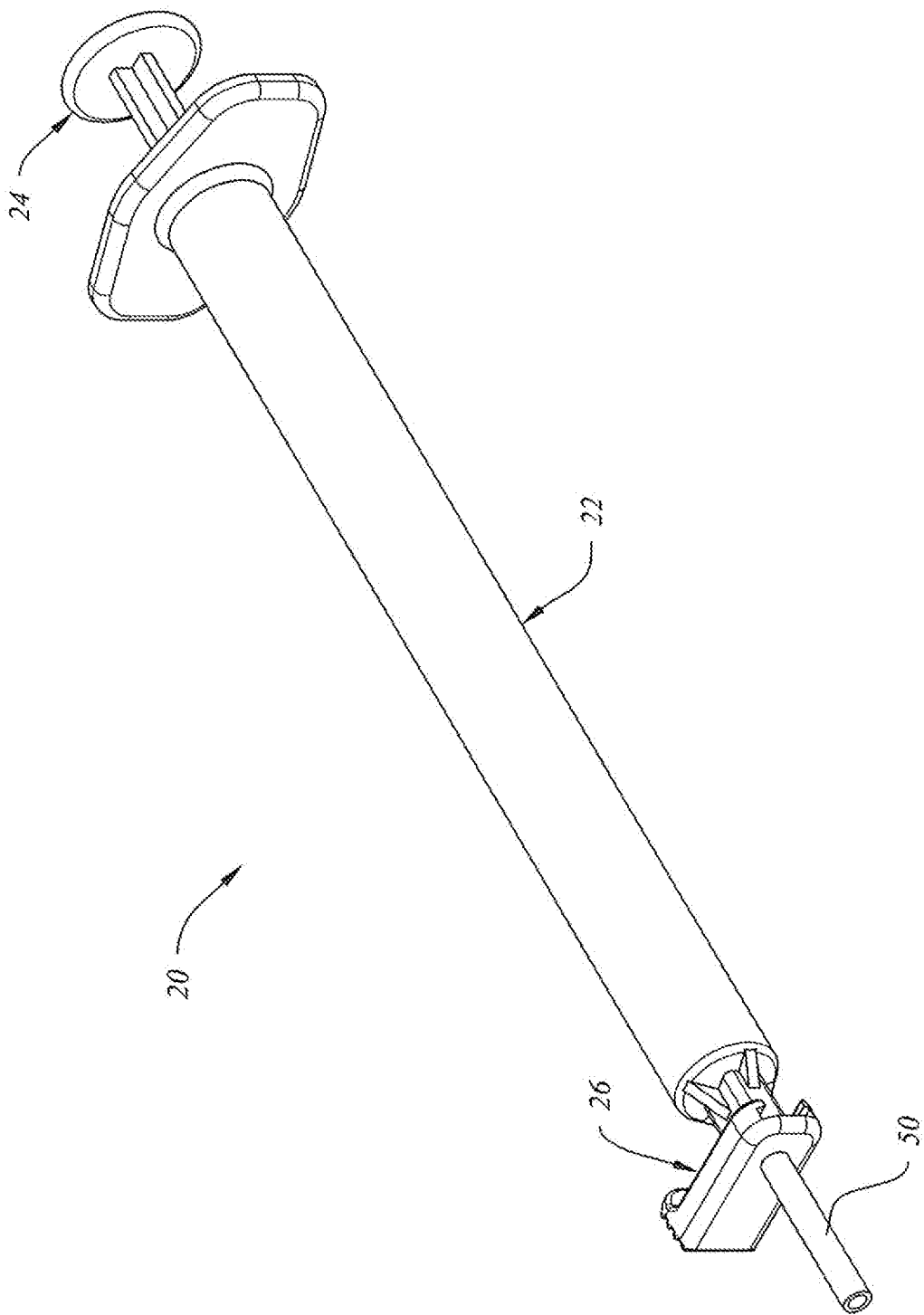
FIG. 1 is a front perspective view of one satisfactory embodiment of the safety syringe of the invention with the needle cap in place.
Figure 2:
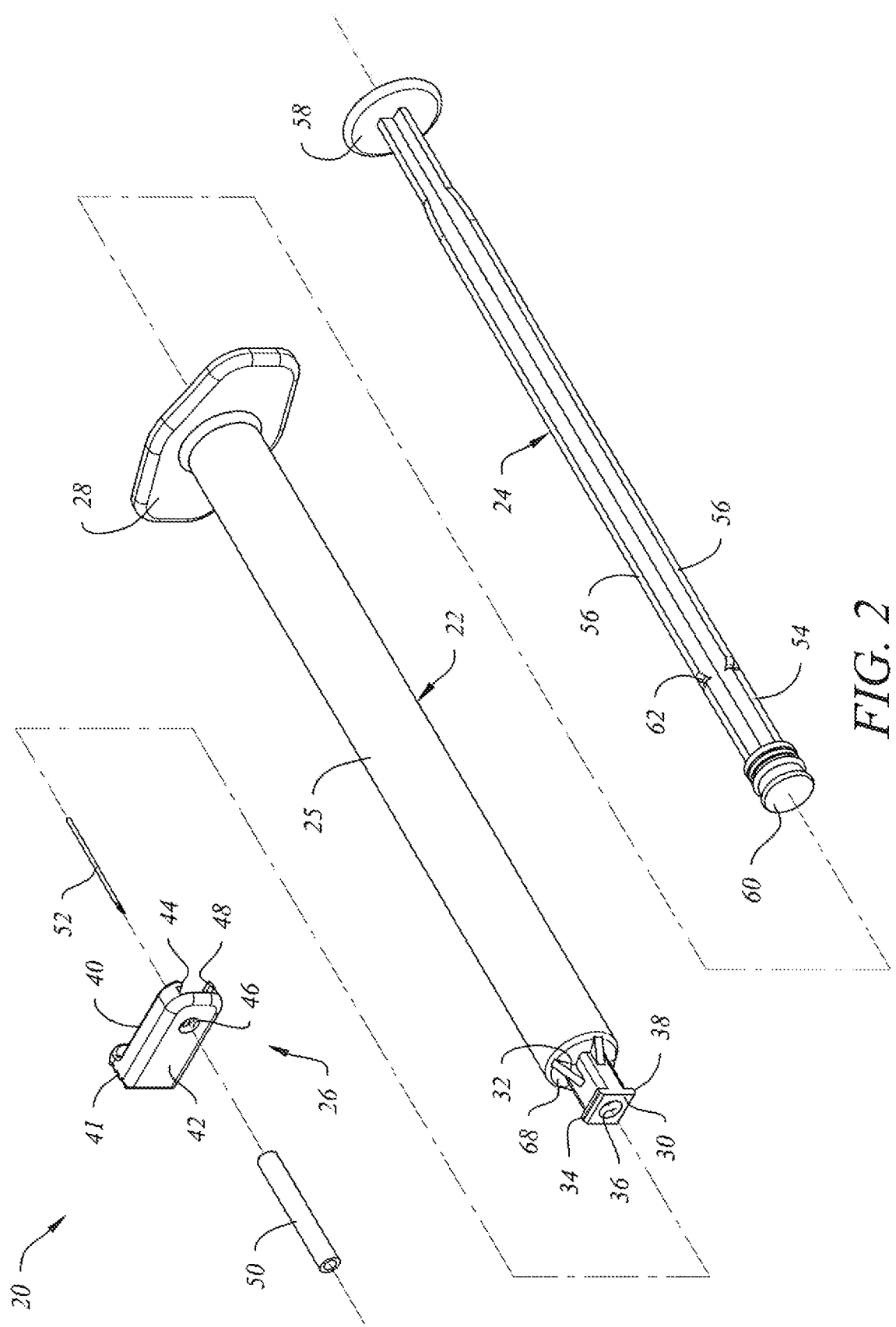
FIG. 2 is an exploded view of the safety syringe of FIG. 1.

Referring to FIG. 1 of the accompanying drawings, syringe 20 comprises barrel 22, plunger 24, slide member 26 and selectively removable needle cap 50. Referring more particularly to FIGS. 2-11, barrel 22 further comprises cylindrical body 25, laterally extending flange member 28, nose end 30, slide support structure 32 attached to tapered section 68 of barrel 22, aperture 36 communicating with the inside of body 25, and upper and lower slide support rails 34, 38. Plunger 24 further comprises plunger handle 54 with a plurality of arcuately spaced apart, longitudinally extending guide ribs 56, rear end cap 58, and an elastomeric plunger seal 60 that provides a fluid seal with the inside wall of the barrel when inserted into cylindrical body 25 of barrel 22 through a rear opening surrounded by flange member 28. Slide member 26 further comprises back side 40, laterally facing touch pad 41, front face 42 with aperture 46, and upper and lower transverse rails 44, 48, respectively, on back side 40 that are slidably engageable with upper and lower slide support rails 34, 38 on nose end 30 of slide support structure 32. Needle 52 desirably has a base end that is inserted through aperture 36 and attached in fixed relation to the inside of slide support structure 32 of barrel 22. The tip end of needle 52 is also inserted through aperture 46 of slide member 26 to project forwardly of slide member 26 when syringe 20 is fully assembled. Selectively releasable end cap 50 is desirably provided to protect the front tip of needle 52 from being blunted or otherwise damaged prior to use.

End cap 50 is desirably configured to be insertable through aperture 46 of slide member 26 and to frictionally engage aperture 36 of barrel 22 so that slide member 26 is prevented from sliding relative to nose end 30 of slide support structure 32 prior to use of syringe 20. Notches 62 are optionally provided in plunger handle 54 to facilitate breaking the plunger handle after withdrawing it to a point where notches 62 are evenly aligned with the rear opening of barrel 28 (inside flange member 28 in the embodiment shown in FIG. 2). This provides additional assurance that syringe 20 cannot be reused after needle 52 is bent by repositioning slide member 26 relative to slide support structure 32.

Figure 9:
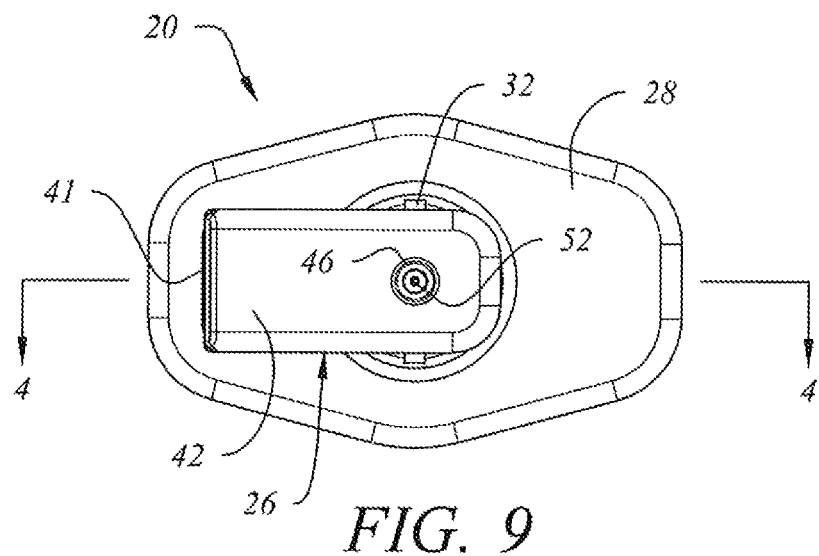
FIG. 9 is a left side elevation view of the safety syringe of FIG. 3.

Referring to FIGS. 3, 4 and 9, syringe 20 of the invention is shown with end cap 50 (FIG. 1) removed. As is visible in FIG. 4, needle 52 is disposed in fixed relation to barrel 22 using adhesive deposited in the annular space provided interiorly of nose end 30 of slide support structure 32 of barrel 22, and provides fluid communication between the front tip of needle 52 and the variable volume fluid chamber 70 that is disposed between plunger seal 60 and needle 52.

Figure 10:
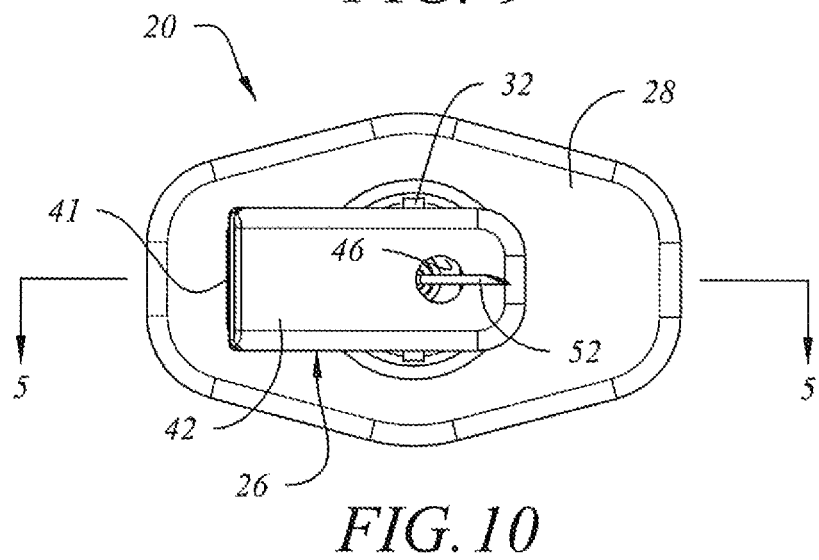
FIG. 10 is a left side elevation view of the safety syringe of FIG. 5.

Referring to FIGS. 5, 6 and 10, plunger 24 is fully depressed inside barrel 25 by thumb pressure applied to end cap 58 of plunger 24 and all liquid medicine previously contained in variable volume chamber 70 (FIG. 5) of barrel 22 has been dispensed through needle 52 as plunger seal 60 contacts the inside wall of cooperatively tapered section 68 of barrel 22. Following injection and withdrawal of needle 52 from a patient or infusion site, the safety aspect of syringe 20 is activated by applying manual pressure (preferably digital pressure) to begin moving slide member 26 (FIG. 2) including front face 42, back side 40 and aperture 46 laterally relative to barrel 22, causing needle 52 to bend as it is contacted and its bending resistance is over pressured by the trailing wall of aperture 46 as shown in FIG. 6.

Figure 11:
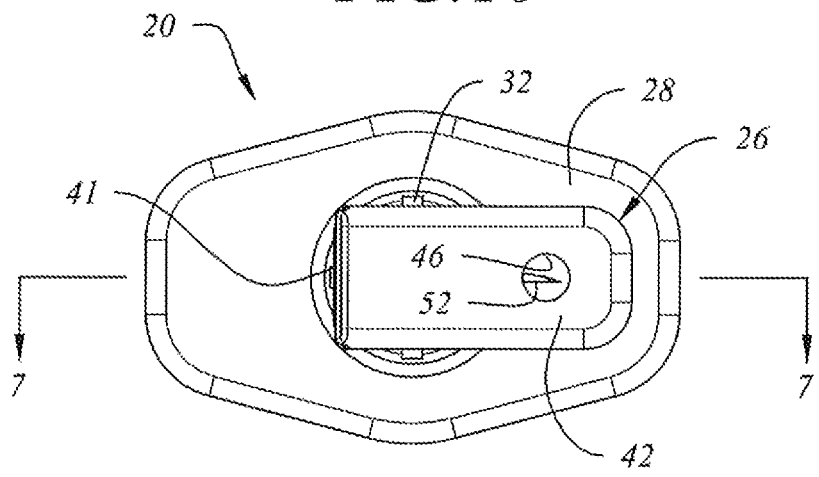
FIG. 11 is a front elevation view of the safety syringe of FIG. 7.
Figure 14:
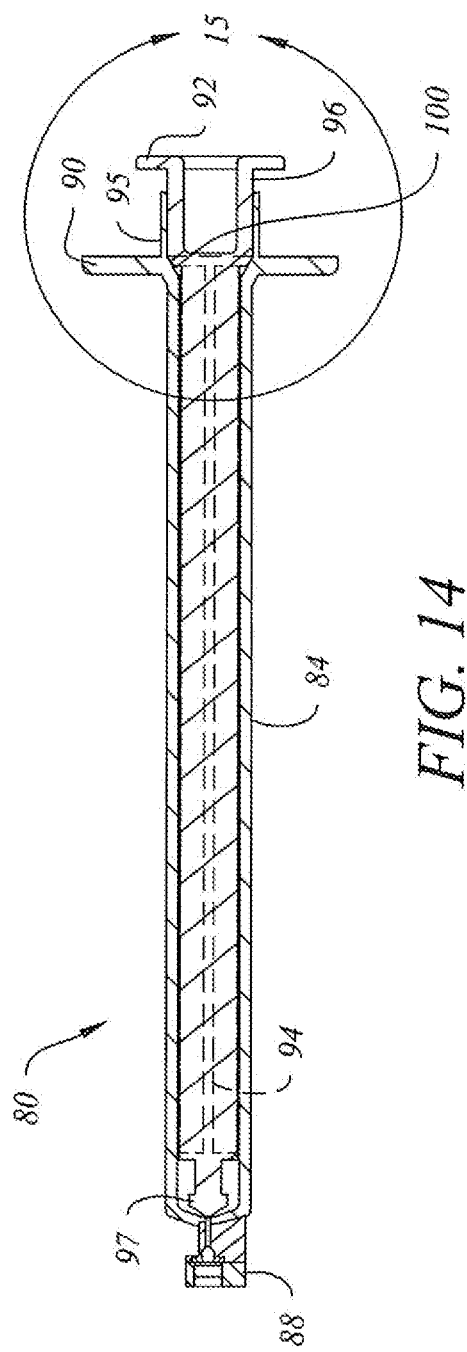
FIG. 14 is a cross-sectional plan view of the embodiment of FIG. 13, with the plunger fully depressed inside the plunger.
Figure 15:
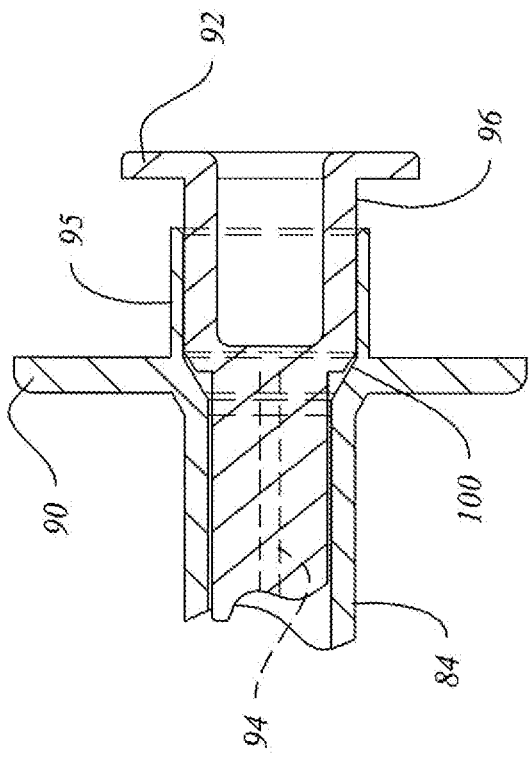
FIG. 15 is an enlarged detail view taken from FIG. 14.

Referring to FIGS. 7, 8 and 11, pressure is continually applied to touch surface 41, and the needle tip eventually recedes through aperture 46 until needle 52 is bent transversely at elbow 53 to an extent where the needle tip is disposed in a position that is transverse to the longitudinal axis through syringe barrel 22 and is protected from accidental contact with the user or a patient or bystander behind front face 42 of the slide member to help prevent accidental needle sticks. The slide member, the diameter of aperture 46 and the length of needle 52 are all cooperatively configured to insure that the sharp tip end of needle 52 is fully behind aperture 46 before the back side of touch surface 41 contacts nose end 30 or slide support structure 32.

Another embodiment of the invention is disclosed in relation to syringe body and plunger combination 80 as depicted in FIGS. 12-15. In this embodiment of the invention, which is presented for illustrative purposes and is not intended to represent a fully assembled, functional syringe, no plunger seal is depicted as installed on the front end of plunger handle 94. Referring to FIGS. 12-15, plunger handle 94 is shown inserted through collar 95 and flange member 90 of barrel 82, which further comprises a slide support structure 88 formed on the forwardly extending portion of cylindrical side wall 84. Because no plunger seal is present, plunger seal support member 97 is visible. End cap 92 of plunger handle 92 preferably further comprises a cylindrical plug 96 having an outside diameter that is sized to frictionally engage the inside wall of collar 95 when plunger handle 94 is depressed inside barrel 82 until the forwardly facing shoulder of plug 96 abuts against inwardly tapered shoulder 100 of barrel 82.

Figure 16:
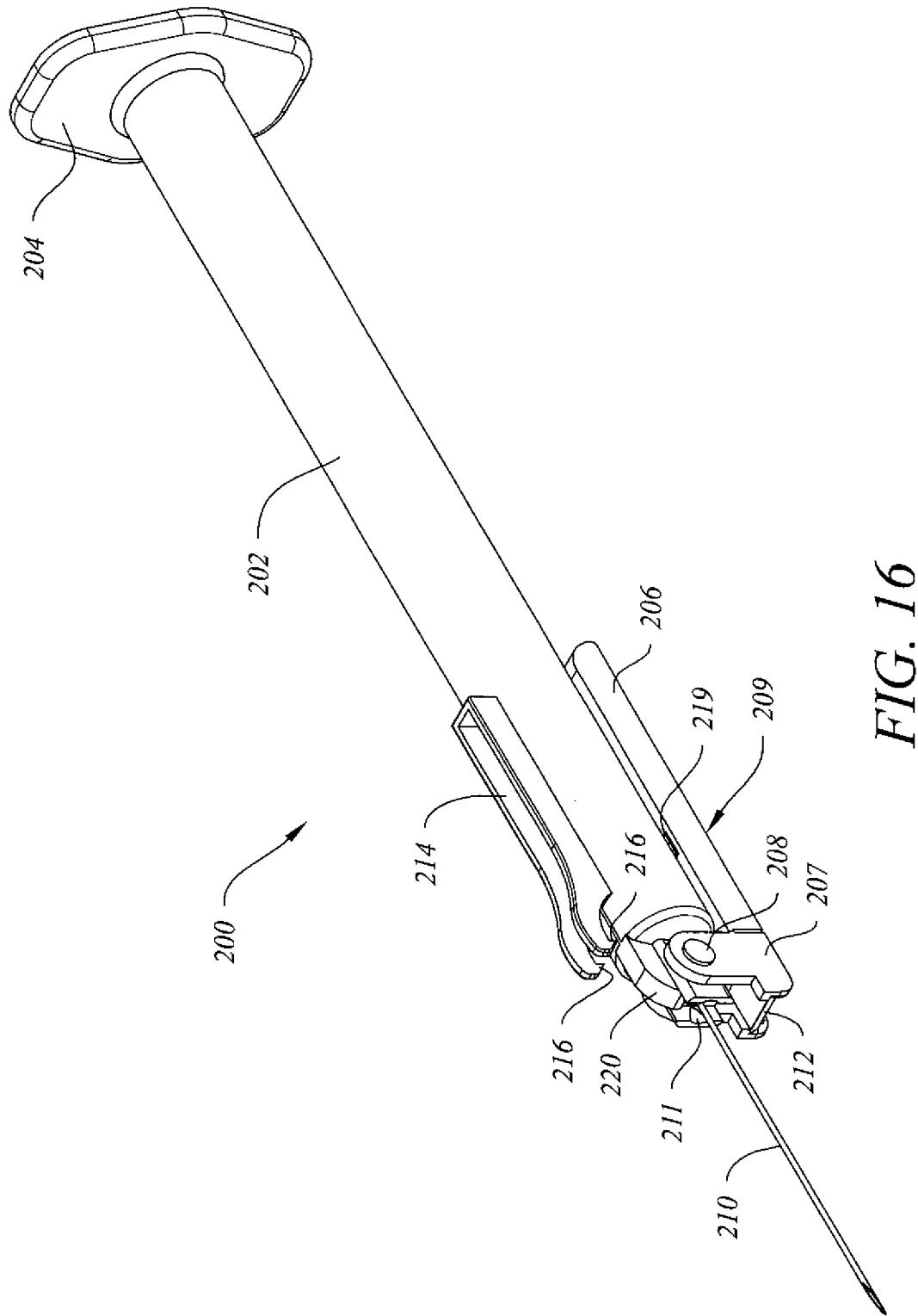
FIG. 16 is a top front perspective view of another embodiment of a safety syringe of the invention (excluding the plunger) in which the actuator portion of a needle redirection device is underlying the syringe barrel and is pivotably connected to the front portion of the barrel behind a forwardly extending needle, with the needle bevel facing upwardly as it would be during an injection.

Another embodiment of the invention is disclosed in relation to FIGS. 16-20 of the drawings. In these drawing figures, no plunger is shown; although it should be understood by the reader that a plunger such as plunger 24 described above in relation to the embodiment of FIGS. 1-5, 7 or another similarly effective plunger is satisfactory for use in combination with syringe barrel assembly 200 as depicted in FIGS. 16-20. Referring to FIG. 16, syringe barrel assembly 200 comprises substantially cylindrical barrel 202 having an open rear end surrounded by finger flange 204. Needle 210 is supported by and projects forwardly from needle holder 211, which is disposed adjacent to nose block 220 at the front of syringe barrel 202. As depicted in FIG. 16, the bevel at the tip end of needle 210 is facing upwardly in the position it would be following an injection. This embodiment of the invention is preferred for use with longer needles, ranging up to about 1.5 inches or more in length.

Needle redirecting device 209 satisfactorily comprises actuator 206 and pivotable attachment bracket 207. Oppositely disposed cylindrical bosses 208 project laterally through cooperatively configured apertures in each of two spaced-apart lobes of pivotable attachment bracket 207 to support needle redirecting device 209 in pivotable relation to needle holder 211. Needle holder 211 further comprises bearing surface 212 that contacts the forwardly projecting shaft of needle 210 as further discussed below in relation to FIG. 19. Cradle 214 is desirably mounted on the outside wall of barrel 202 parallel to the longitudinal axis through needle 210. Cradle 214 satisfactorily comprises side and end walls defining a longitudinally extending slot that is open at the front end to receive needle 210. Oppositely disposed hook members 216 are provided for use in securing pivotable attachment bracket 207 and actuator 206 in a forwardly facing position to hold needle 210 in a protected position inside cradle 214 following bending of needle 210 as discussed in relation to FIGS. 18-20 below. Actuator 206 and pivotable attachment bracket 207 are desirably unitarily molded from a polymeric resin although other similarly effective structures and apparatus for attaching actuator 206 to pivotable attachment bracket 207 or for otherwise pivotably connecting actuator 206 to syringe barrel assembly 200 can likewise be used.

Figure 17:
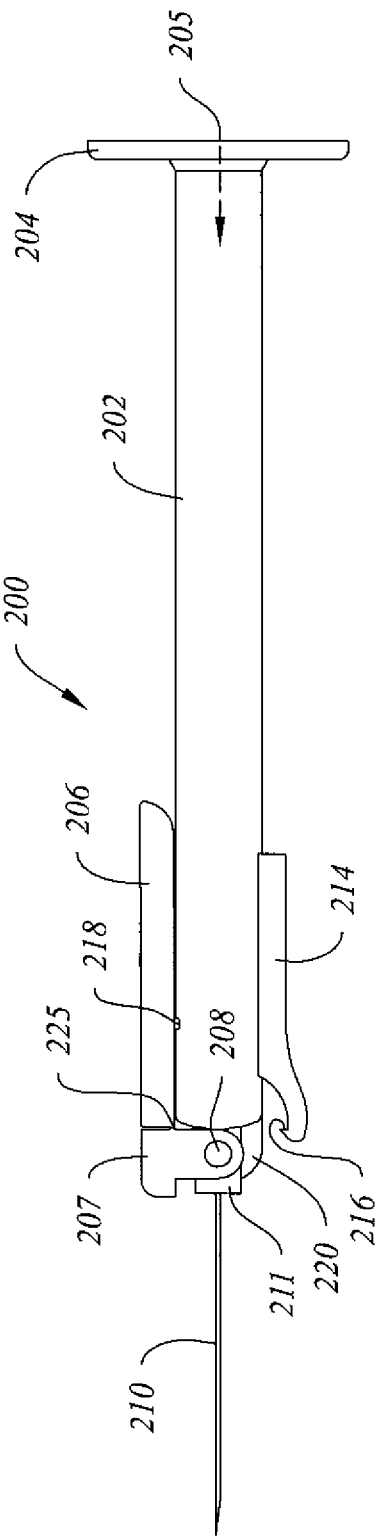
FIG. 17 is an elevation view of the safety syringe of FIG. 16 that is rotated 180° around its longitudinal axis so that the actuator portion of the needle redirection device is facing upwardly and the needle bevel is facing downwardly.
Figure 18:
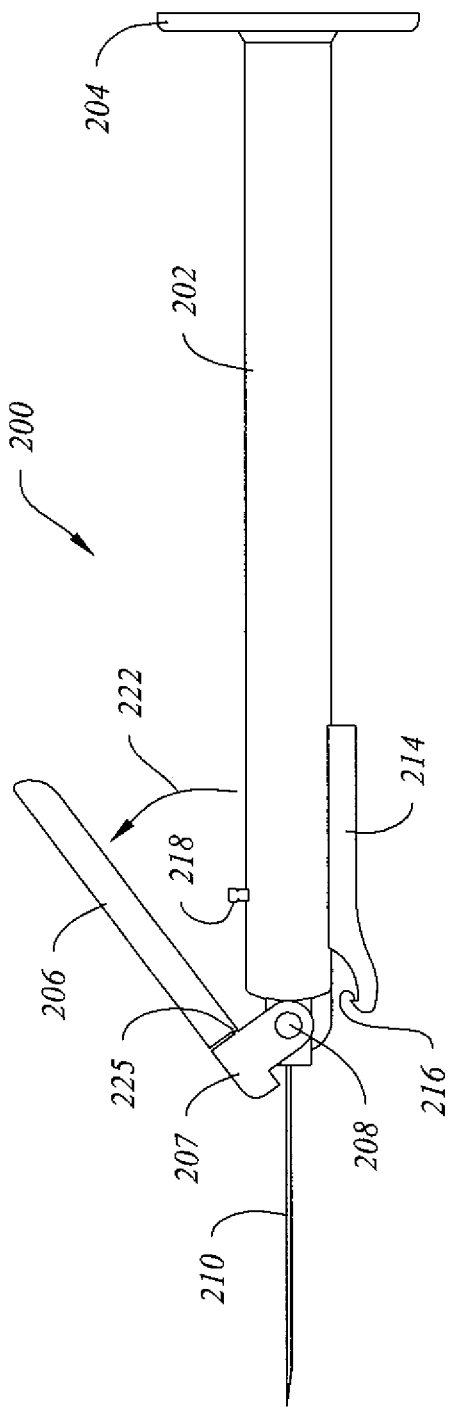
FIG. 18 is an elevation view as in FIG. 17 but with the actuator lifted away from the syringe barrel and rotated around a transverse axis to an intermediate position just prior to contacting the needle, with the needle still projecting forwardly from the barrel as it would be following an injection.

Referring to FIG. 17, barrel 202 of syringe barrel assembly 200 is inverted from the position depicted in FIG. 16, so that cradle 214 and the bevel at the tip end of needle 210 are facing down and actuator 206 is disposed above and parallel to syringe barrel 202. Referring next to FIG. 18, actuator 206 is pushed upwardly and away from frictional catch 218, and is being pivoted around oppositely disposed bosses 108 (only one of which is visible in FIG. 18) in an arc that is indicated by arrow 222. In FIG. 18, actuator 206 is in an intermediate position and is not yet in contact with the shaft of needle 210, which remains in a forwardly projecting position relative to barrel 202.

Referring next to FIG. 19, actuator 206 is pivoted further around bosses 208 so that the length of the arc indicated by arrow 222 has lengthened relative to that shown in FIG. 18 and bearing surface 212 has contacted and bent the shaft of needle 210 downwardly relative to its first position. Referring next to FIG. 20, actuator 206 is pivoted around bosses 208 to a second and final position in which it is rotated a full 180° from the first position, and in which needle 210 is bent to a rearwardly facing position with the needle tip disposed within cradle 214. In the position shown in FIG. 20, a square shoulder on the trailing side of bearing surface 212 is fully engaged with and restrained by opposed hooks 216 (better seen in FIG. 19) of cradle 214.

When actuator 206 of needle redirection device 209 (FIG. 16) is restrained in the position shown in FIG. 20, the shaft of needle 210 is bent to a position substantially parallel to syringe barrel 202 where the needle tip is facing rearwardly and is held inside the slot formed between the side walls and end wall of cradle 214. The patient, user and any bystander or subsequent handler of syringe barrel assembly 200 are thereby protected from accidental needle stick injuries and any resultant risk of infection. Living hinge 225 is desirably provided between actuator 206 and pivotable attachment bracket 207 to aid in preventing a user from accidentally unlatching pivotable attachment bracket 207 and the bent needle 210 from cradle 214 after the tip end of needle 210 is disposed inside cradle 214.

Depending upon the configuration, travel path and range of movement of the needle redirection member, the needle tip of the subject safety syringe can be redirected through an arc ranging from about 80 degrees to about 185 degrees from its first forwardly facing position, with second positions that are either substantially transverse to, or facing oppositely from, the first positions being generally preferred.

As will be appreciated by those of skill in the art upon reading this disclosure, the disclosed safety syringe provides an effective means for protecting users, patients and bystanders from an accidental needle stick injuries and the possibility of resultant complications and need for medical treatment due to the potential for contamination by infectious blood-borne pathogens from the patient following an injection. All parts of the device except for the elastomeric plunger seal and the needle can be made of molded plastic without the need for close manufacturing tolerances required by other syringe configuration, and the device is easily assembled. Upon activation of a needle redirection device such as the slide member or actuator disclosed herein following an injection, the syringe is rendered ineffective for future use and can be safely disposed of without need for reattaching the needle cap. If desired, one or more cooperatively configured projections and detents or other similarly useful elements or mechanisms can be provided on the slide member and the slide support structure, or on the syringe barrel and the actuator to maintain the position of the slide member or actuator prior to completion of the injection and after the needle is bent.

Other alterations and modifications of the invention will likewise become apparent to those of ordinary skill in the art upon reading this specification in view of the accompanying drawings, and it is intended that the scope of the invention disclosed herein be limited only by the broadest interpretation of the appended claims to which the inventor(s) and/or Applicant are legally entitled.

What is claimed is:

1. A safety syringe comprising:
   a barrel having a nose end further comprising a slide support structure;
   a needle connected to the nose end of the barrel, the needle having a forwardly extending end comprising a needle tip;
   a plunger slidably disposed inside the barrel, the plunger further comprising a plunger seal establishing a fluid seal between the plunger and an inside wall of the barrel; and
   a needle redirection device further comprising a slide member attached to the slide support structure, the slide member further comprising an aperture through which the needle projects forwardly from the nose end of the barrel and a laterally facing touch surface that initiates transverse sliding movement of the slide member relative to the slide support structure upon the application of digital pressure to the touch surface following an injection and removal of the needle from a patient, wherein said transverse sliding movement and the continued application of digital pressure to the touch surface causes the needle to bend from a first position that is coaxially aligned with the barrel to a second position in which the needle tip is substantially transverse to the barrel and is disposed in a protected position behind the slide member.

2. The safety syringe of claim 1 wherein the barrel is configured to administer injections or infusions of not more than about 1 mL.

3. The safety syringe of claim 1 wherein the needle has a nominal length ranging between about 4 mm and about 13 mm.

4. The safety syringe of claim 3 wherein the needle has a nominal length ranging between about 4 mm and about 8 mm.

5. The safety syringe of claim 1 wherein the needle has a nominal gauge ranging between about 28 and about 32.

6. The safety syringe of claim 1 configured as an insulin syringe.

7. The safety syringe of claim 1 wherein the needle is disposed in fixed relation to the nose end of the barrel.

8. The safety syringe of claim 7 wherein the needle is disposed in fixed relation to a needle holder seated inside the nose end of the barrel.

9. A safety syringe comprising:
   a needle suitable for use in administering a subcutaneous injection, the needle having a forwardly extending tip end and a gauge in the range of from about 28 to 32;
   a longitudinally extending barrel with a nose end; and
   a needle redirection device further comprising a slide member attached to the nose end, the slide member having a touch surface and a forwardly facing aperture coaxially aligned with the longitudinally extending barrel, through which aperture the needle projects forwardly of the slide member in coaxial alignment with the barrel prior to and during the injection;
   the slide member being configured to slide transversely relative to the nose end of the barrel in response to the application of manual pressure to the touch surface of the slide member following the injection to contact and bend the needle until the needle tip is transverse to the longitudinally extending barrel and the tip end of the needle is disposed behind and is protected by the slide member.

10. The syringe of claim 9 wherein the nose end comprises a slide support structure to which the slide member is attached so as to permit relative slidable movement between the slide member and the slide support structure in a direction transverse to the longitudinally extending barrel.

11. The syringe of claim 10, further comprising a selectively removable needle cap that frictionally engages at least one of the slide support structure and the slide member, and restricts lateral movement of the slide member relative to the coaxially aligned needle and the longitudinally extending barrel prior to the injection.

12. The syringe of claim 9 wherein the needle has a length in the range of from about 4 to about 13 mm.

13. The syringe of claim 12 wherein the needle has a length in the range of from about 4 to about 8 mm.

14. The syringe of claim 9 wherein the aperture has an inside diameter, the needle has an outside diameter, and the inside diameter of the aperture is greater than the outside diameter of the needle.

15. A safety syringe comprising:
   a barrel;
   a plunger slidably disposed inside the barrel;
   a hypodermic needle supported by a needle holder disposed at the front of the barrel, the hypodermic needle having a tip end projecting forwardly from the barrel prior to and during use of the safety syringe to administer an injection;
   a needle redirecting device comprising an actuator pivotably connected at the front of the barrel that is selectively activated by a user following the injection to bend a shaft portion of the needle from a first position wherein the tip end projects forwardly from the barrel and is moved by the actuator through an arc of about 180 degrees to a second position wherein the tip end faces rearwardly; and
   a cradle in which the tip end is retained in the rearwardly facing second position and protected from contact following use.

16. The safety syringe of claim 15 wherein the needle redirecting device comprises a pivotable attachment bracket to which the actuator is pivotably connected by oppositely disposed, laterally extending cylindrical bosses.

17. The safety syringe of claim 15 wherein the hypodermic needle ranges from about 0.5 up to about 1.5 inches in length.

18. The safety syringe of claim 15 wherein the needle holder supports a rearwardly facing base portion of the needle in substantially fixed relation to the barrel.

19. The safety syringe of claim 15 wherein the cradle is disposed in substantially fixed relation to a side wall portion of the barrel.

20. The safety syringe of claim 15 wherein the cradle further comprises at least one hook configured to latch onto the needle redirecting device when the actuator is pivotably rotated so that the rearwardly facing tip end of the needle is disposed inside the cradle.

21. The safety syringe of claim 15 wherein a rear portion of the plunger is frictionally engageable with an inwardly facing side wall portion of the barrel.

\* \* \* \* \*